United States Patent
Chen et al.

(12)

(10) Patent No.: US 11,458,164 B2
(45) Date of Patent: Oct. 4, 2022

(54) ***STREPTOCOCCUS THERMOPHILUS* STRAIN ST4 AND ITS EFFICACIES OF ANTI-INFLAMMATION AND CANCER PREVENTION**

(71) Applicant: Syngen Biotech. Co., Ltd., Tainan (TW)

(72) Inventors: Wei-Jen Chen, Tainan (TW);
Shiuan-Huei Wu, Tainan (TW);
Chiau-Ling Gung, Tainan (TW);
Yu-Lun Tsai, Tainan (TW)

(73) Assignee: SYNGEN BIOTECH CO., LTD., Tainan (TW)

( * ) Notice: Subject to any disclaimer, the term of this patent is extended or adjusted under 35 U.S.C. 154(b) by 0 days.

(21) Appl. No.: 16/937,017

(22) Filed: Jul. 23, 2020

(65) Prior Publication Data

US 2021/0023130 A1 Jan. 28, 2021

(30) Foreign Application Priority Data

Jul. 24, 2019 (TW) .................................. 108126266

(51) Int. Cl.
*A01N 63/00* (2020.01)
*A61K 35/00* (2006.01)
*A61P 35/00* (2006.01)
*C12N 1/20* (2006.01)

(52) U.S. Cl.
CPC .............. *A61K 35/00* (2013.01); *A61P 35/00* (2018.01); *C12N 1/20* (2013.01); *A61K 2035/115* (2013.01)

(58) Field of Classification Search
CPC ...................................................... A61K 35/00
See application file for complete search history.

(56) References Cited

U.S. PATENT DOCUMENTS

| 7,253,333 B2* | 8/2007 | Tanaka | A01K 67/0339 |
| | | | 800/10 |
| 2006/0094649 A1* | 5/2006 | Keogh | C07K 14/71 |
| | | | 424/185.1 |

OTHER PUBLICATIONS

Marcial et al., "Exopolysaccharide-producing *Streptococcus thermophilus* CRL1190 reduces the inflammatory response caused by Helicobacter pylori", Beneficial Microbes, 2017, pp. 451-461, 8(3).

Rodriguez et al., "Therapeutic effect of *Streptococcus thermophilus* CRL 1190-fermented milk on chronic gastritis", World J Gastroenterol, Apr. 7, 2010, pp. 1622-1630, 16(13).

Zhong et al., "Emerging roles of lactic acid bacteria in protection against colorectal cancer", World J Gastroenterol, Jun. 28, 2014, pp. 7878-7886, 20(24).

* cited by examiner

*Primary Examiner* — Albert M Navarro
(74) *Attorney, Agent, or Firm* — Birch, Stewart, Kolasch & Birch, LLP

(57) ABSTRACT

The present invention provides a novel *Streptococcus thermophilus* strain ST4, and its use in manufacturing a medicament and/or food composition for treating and/or preventing an inflammatory disease and/or a cancer.

4 Claims, 4 Drawing Sheets
Specification includes a Sequence Listing.

Analysis results of VITEK identification system

FIG.2

SEQUENCE LISTING

<160> NUMBER OF SEQ ID NOS: 1

<210> SEQ ID NO 1
<211> LENGTH: 1496
<212> TYPE: DNA
<213> ORGANISM: Streptococcus thermophilus

<400> SEQUENCE: 1

```
gacgaacgct ggcggcgtgc ctaatacatg caagtagaac gctgaagaga ggagcttgct      60
cttcttggat gagttgcgaa cgggtgagta acgcgtaggt aacctgcctt gtagcggggg     120
ataactattg gaaacgatag ctaataccgc ataacaatgg atgacacatg tcatttattt     180
gaaagggca attgytccac tacaagatgg acctgcgttg tattagctag taggtgaggt      240
aatggctcac ctaggcgacg atacatagcc gacctgagag ggtgatcggc caatgggatg     300
agaacgccc agactcctac gggaggcagc agtagggaat cttcggcaat ggggcaacc       360
ctgaccgagc aacgccgcgt gagtgaagaa ggttttcgga tcgtaaagct ctgttgtaag     420
tcaagaacgg gtgtgagagt ggaaagttca cactgtgacg gtagcttacc agaaagggac     480
ggctaactac gtgccagcag ccgcggtaat acgtaggtcc cgagcgttgt ccggatttat     540
tgggcgtaaa gcgagcgcag gcggtttgat aagtctgaag ttaaaggctg tggctcaacc     600
atagttcgct ttggaaactg tcaaacttga gtgcagaagg ggagagtgga attccatgtg     660
tagcggtgaa atgcgtagat atatggagga acaccggtgg cgaaagcggc tctctggtct     720
gtaactgacg ctgaggctcg aaagcgtggg gagcgaacag gattagatac cctggtagtc     780
cacgccgtaa acgatgagtg ctaggtgttg gatcctttcc gggattcagt gccgcagcta     840
acgcattaag cactccgcct ggggagtacg accgcaaggt tgaaactcaa aggaattgac     900
gggggcccgc acaagcggtg gagcatgtgg tttaattcga agcaacgcga agaaccttac     960
caggtcttga catcccgatg ctatttctag agatagaaag ttacttcggt acatcggtga    1020
caggtggtgc atggttgtcg tcagctcgtg tcgtgagatg ttgggttaag tcccgcaacg    1080
agcgcaaccc ctattgttag ttgccatcat tcagttgggc actctagcga gactgccggt    1140
aataaaccgg aggaaggtgg ggatgacgtc aaatcatcat gccccttatg acctgggcta    1200
cacacgtgct acaatggttg gtacaacgag ttgcgagtcg gtgacggcga gctaatctct    1260
taaagccaat ctcagttcgg attgtaggct gcaactcgcc tacatgaagt cggaatcgct    1320
agtaatcgcg gatcagcacg ccgcggtgaa tacgttcccg ggccttgtac acaccgcccg    1380
tcacaccacg agagtttgta acacccgaag tcggtgaggt aaccttttgg agccagccgc    1440
ctaaggtggg acagatgatt ggggtgaagt cgtaacaagg tagccgtatc ggaagg        1496
```

STREPTOCOCCUS THERMOPHILUS STRAIN ST4 AND ITS EFFICACIES OF ANTI-INFLAMMATION AND CANCER PREVENTION

BACKGROUND OF THE INVENTION

Field of the Invention

The present invention relates to a novel *Streptococcus thermophilus* strain and, in particular, to a use of a novel *Streptococcus thermophilus* strain for treating and/or preventing an inflammatory disease and/or a cancer.

Description of the Prior Art

According to estimates, about 20% of colorectal cancer is caused by genetics, and about 80% of colorectal cancer is contributed by factors such as chronic intestinal inflammation, intestinal bacterial flora, etc.

Intestinal inflammation can initiate intestinal tumor formation and accelerate tumor growth rate. For example, the cell wall component of Gram-negative bacteria, Lipopolysaccharide (LPS), promotes the growth and spread of colorectal cancer cells by promoting an inflammatory response. Scientific research has confirmed that the inhibition of intestinal inflammation can effectively prevent colorectal cancer and slow down the disease progression of colorectal cancer.

Injection of the mutagenic agent azoxymethane (AOM) to mice and addition of dextran sulfate sodium (DSS) that destroys the large intestinal epithelial cells into mice drinking water cause the intestinal inflammation, and will result in colorectal cancer in about two months. The clinical features of such colorectal cancer caused by the AOM/DSS mouse model are very consistent with human colorectal cancer, such as weight loss, hyperplasia of intestinal polyps, etc. Moreover, the severity of intestinal inflammation in this model can be simply judged by the gut weight/length ratio, the value of which is proportional to the degree of intestinal inflammation so that this model has been widely used to study the progress of intestinal inflammation and colorectal cancer.

The imbalance of intestinal flora is a risk factor for induction of colorectal cancer. At present, a variety of bacteria have been found obviously increased in the intestine of patients with colorectal cancer, such as Enterobacteriaceae, *Escherichia coli*, and *Streptococcus*. The patients who had been infected with *Streptococcus* gallolyticus or *Streptococcus infantarius* have a significantly high probability of developing colorectal cancer. The studies further confirmed that the cell wall component of *Streptococcus bovis* and the protein component of *Streptococcus infantarius* cell wall can effectively induce cells, such as THP-1, to release the proinflammatory cytokines TNF-α and IL-8, and promote the formation of aberrant crypt foci in colorectal precancerous lesions, showing that some strains of *Streptococcus* can induce colorectal carcinogenesis through the inflammatory reaction.

*Streptococcus thermophilus* is a common probiotic species, and is widely used in the production of fermented dairy products. Although the scientific literature has reported that *Streptococcus* may be associated with intestinal inflammation and colorectal cancer, the characteristics and abilities of different strains are variable. Therefore, it is necessary to develop a *Streptococcus thermophilus* strain that is safe and can suppress inflammation and colorectal cancer.

SUMMARY OF THE INVENTION

The present invention i provides a novel *Streptococcus thermophilus* strain ST4., which is isolated from the microbial flora of raw milk and is different from the existing known strains. The novel *Streptococcus thermophilus* strain of the present invention provides the efficacy in treating or preventing inflammatory diseases or colorectal cancer.

In one aspect, the present invention provides an isolated *Streptococcus thermophilus* strain ST4 (*Streptococcus thermophilus* ST4), which is deposited at Deutsche Sammlung von Mikroorganismen and Zellkulturen GmbH with deposit number DSM33165 on May 28, 2019.

In another aspect, the present invention provides a composition comprising an effective amount of the *Streptococcus thermophilus* strain ST4, which may be live or dead. The composition may be prepared in the form of a food for treating or preventing an inflammatory disease of a subject.

In yet aspect, the present invention provides a method for treating or preventing an inflammatory disease or a cancer, which comprises administering to a subject in need thereof an effective amount of the *Streptococcus thermophilus* strain ST4.

In one particular example of the invention, the *Streptococcus thermophilus* strain ST4 in the compositon is live or dead. In particular example of the invention, the the *Streptococcus thermophilus* strain ST4 in the compositon is dead.

In one example of the invention, the composition inhibits the production of TNF-α.

BRIEF DESCRIPTION OF THE DRAWINGS

The foregoing description and the following detailed description of the invention will be better understood when reading in conjunction with the accompanying drawings. For the purpose of illustrating the present invention, currently preferred embodiments are shown in the drawings.

FIG. 2 shows the activities of the heat-inactivated bacteria from *Streptococcus thermophilus* strain ST4, s1, s2, s3 and BCRC13869 strains on inhibition of TNF-α secretion.

DETAILED DESCRIPTION OF THE EMBODIMENTS

Figure 1:
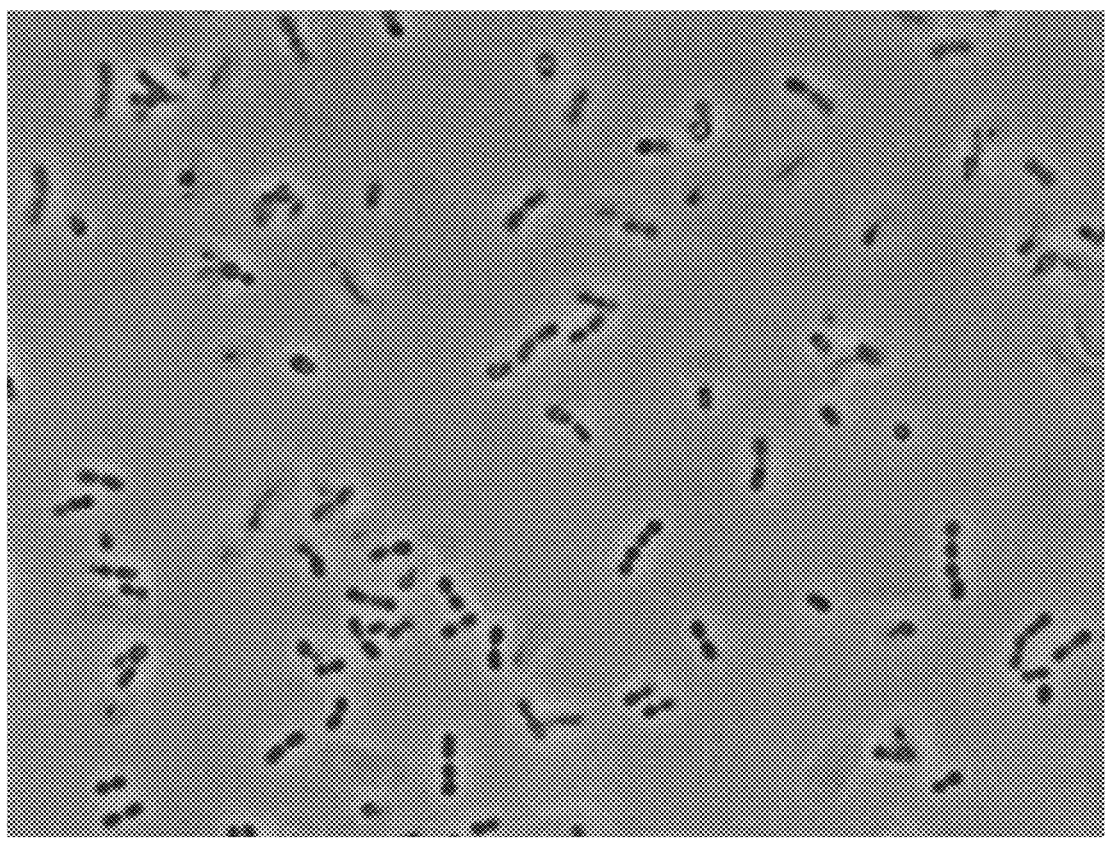
FIG. 1 shows the cell shape of *Streptococcus thermophilus* strain ST4.

Unless otherwise defined, all technical and scientific terms used herein have the same meaning as commonly understood by those skilled in the art to which the present invention pertains. It should be understood that the terminology used herein is for the purpose of describing specific embodiments only, and is not intended to be limiting.

As used herein, the singular forms "a", "an" and "the" include plural references unless explicitly indicated otherwise. Thus, for example, reference to "a sample" includes a plurality of such samples and their equivalents known to those skilled in the art.

As used herein, the term "colony-forming unit" (CFU) is defined as the number of bacterial cells as revealed by microbial production on an agar medium.

As used herein, the term "treatment" refers to the application or administration of one or more active agents to a subject with a disease, disease symptom, or disease propensity, the purpose of which is to treat, cure, relieve, alleviate, alter, remedy, ameliorate, improve, or affect the disease, disease symptom, or disease propensity. For example, as used herein, "treating an inflammatory disease" refers to the reduction of local or systemic excessive inflammatory responses by inhibiting the production of TNF-α in said subject.

As used herein, the term "effective amount" refers to an amount of an active medicament or composition in a subject sufficient to achieve the above therapeutic efficacy. The effective amount can vary, for example, depending on the type or dosage of the medicament or composition and the weight, age, and health status of the subject to be treated.

The present invention provides an isolated *Streptococcus thermophilus* strain ST4, which is deposited at Deutsche Sammlung von Mikroorganismen and Zellkulturen GmbH with deposit number DSM33165 on May 28, 2019.

As used herein, "*Streptococcus thermophilus*" refers to a Gram-positive, homofermentative and facultative anaerobic bacterium, and belongs to *Streptococcus viridans*. Its cytochrome, oxidase and catalase tests are negative, and α-hemolytic test is positive. It has no mobility and no endospores.

The *Streptococcus thermophilus* strain ST4 of the present invention is isolated from microbial flora of raw milk. According to the analysis of bacteriological characteristics, the strain is a Gram-positive bacterium with a spherical or oval shape, in pairs or long chain shape, and without spore formation and motility, grows under anaerobic or aerobic conditions and has no catalase and oxidase activities. The Strain ST4 was identified by 16S rDNA sequence analysis and VITEK identification system, showing that the strain ST4 is a strain of *Streptococcus thermophilus*.

The *Streptococcus thermophilus* strain ST4 according to the present invention may be live or dead, and also includes equivalent strains with the same characteristics and thalli or products derived from said strains.

By using the *Streptococcus thermophilus* strain ST4 as a starting material, any other mutants or derivatives thereof by conventional mutation induction or re-separation techniques, and the mutants or derivatives which retain or enhance the characteristics and efficacies are included in the invention.

In some embodiments, the composition of the present invention has the effect in treating inflammatory diseases. Specifically, as shown in the examples, the composition of the present invention inhibited the secretion of TNF-α from THP-1 cells induced by LPS.

In some embodiments, the composition of the present invention has the effect in inhibiting colorectal tumor hyperplasia. Specifically, as shown in the examples, the composition of the present invention inhibits colorectal cancer caused by mutagen azoxymethane (AOM) and dextran sulfate sodium (DSS), and also has the effect in preventing colorectal tumor proliferation.

The present invention also provides a composition for use as a pharmaceutical, a medicament, a food, an edible product, a food supplement or a medical food comprising an effective amount of the strain ST4 of the present invention. The composition of the invention may be prepared in the form of a pharmaceutical compositon or a food composition.

In the present invention, the composition provides an efficacy in preventing or treating an inflammatory disease in a subject. In the present invention, examples of the inflammatory disease include but not limited to, inflammatory and autoimmune diseases, such as a cancer, Crohn's disease, inflammatory bowel disease (IBD) and inflammatory large intestine disease.

In addition, the composition of the present invention can be used in preventing or treating a cancer in a subject in highly inflammatory conditions, which are also known as having "inflammatory features" and ascending cytokine signaling (e.g., TNF-α). In one embodiment, the cancer is an inflammatory tumor, for example, but not limited to, colorectal cancer, esophageal cancer, gastric cancer, and especially colorectal cancer.

The above description of the present invention and the following embodiments illustrate the content of the present invention, but are not intended to limit the scope of the present invention.

Example 1 Isolation of *Streptococcus thermophilus* Strains ST4

The Strain ST 4 was isolated from the microbial flora of raw milk. The raw milk was added into the MRS broth medium and cultured at 42° C. for 24 hours under anaerobic conditions. Afterwards, the culture was spread on MRS agar plates and incubated at 42° C. for 3 days under anaerobic conditions, and then a single colony appearing on the agar medium was collected and further purified to isolate the Gram-positive, catalase-negative, spherical or oval, and in pair or long chain-shaped, and accordingly it was named as *Streptococcus thermophilus* ST4.

Example 2 the Bacteriological Characteristics of *Streptococcus thermophilus* Strain ST4

The *Streptococcus thermophilus* strain ST4 were characterized to have the following:
(1) Morphological Characteristics:
 (a) Cell shape and Gram stain: After the cells were placed in MRS broth medium and cultured at 42° C. for 24 hours under anaerobic conditions, their appearance under the microscope was spherical or oval, in pairs or long chain-shaped without flagella and Gram stain-positive, as shown in FIG. 1.
 (b) Mobility: No mobility.
 (c) Spore formation: No spore formation.
 (d) Gram stain: Positive.
(2) Characteristics of Culture:
 (a) Medium: MRS broth medium, pH=6.25.
 (b) Culture conditions: at 42° C. under anaerobic or aerobic conditions.
(3) Physiological Characteristics:
 (a) Catalase: negative.
 (b) Oxidase: negative.

Example 3 Strain Identification of *Streptococcus thermophilus* Strain ST4

16S rDNA and VITEK systems were used in strain identification of *Streptococcus thermophilus* strain ST4. Two identification methods were used to ensure the correction of the identification results.

3.1 16S rDNA Sequencing Analysis

The DNA of the *Streptococcus thermophilus* strain ST4 was extracted to amplify the 16S rDNA (ribosomal DNA) fragment, and agarose gel electrophoresis was performed on the resulting PCR product to confirm whether the product conforms to the expected size and perform sequencing. The 16S rDNA sequence of the resulting *Streptococcus thermophilus* strain ST4 was shown as SEQ ID NO:1 and compared with the composite sequence alignment data sets (NCBI blast). The sequence alignment result was closest to *Streptococcus salivarius* subsp. *thermophilus* ATCC 19258$^T$, and the similarity was up to 99.67%.

3.2 Analysis of VITEK Identification System

Figure 2:
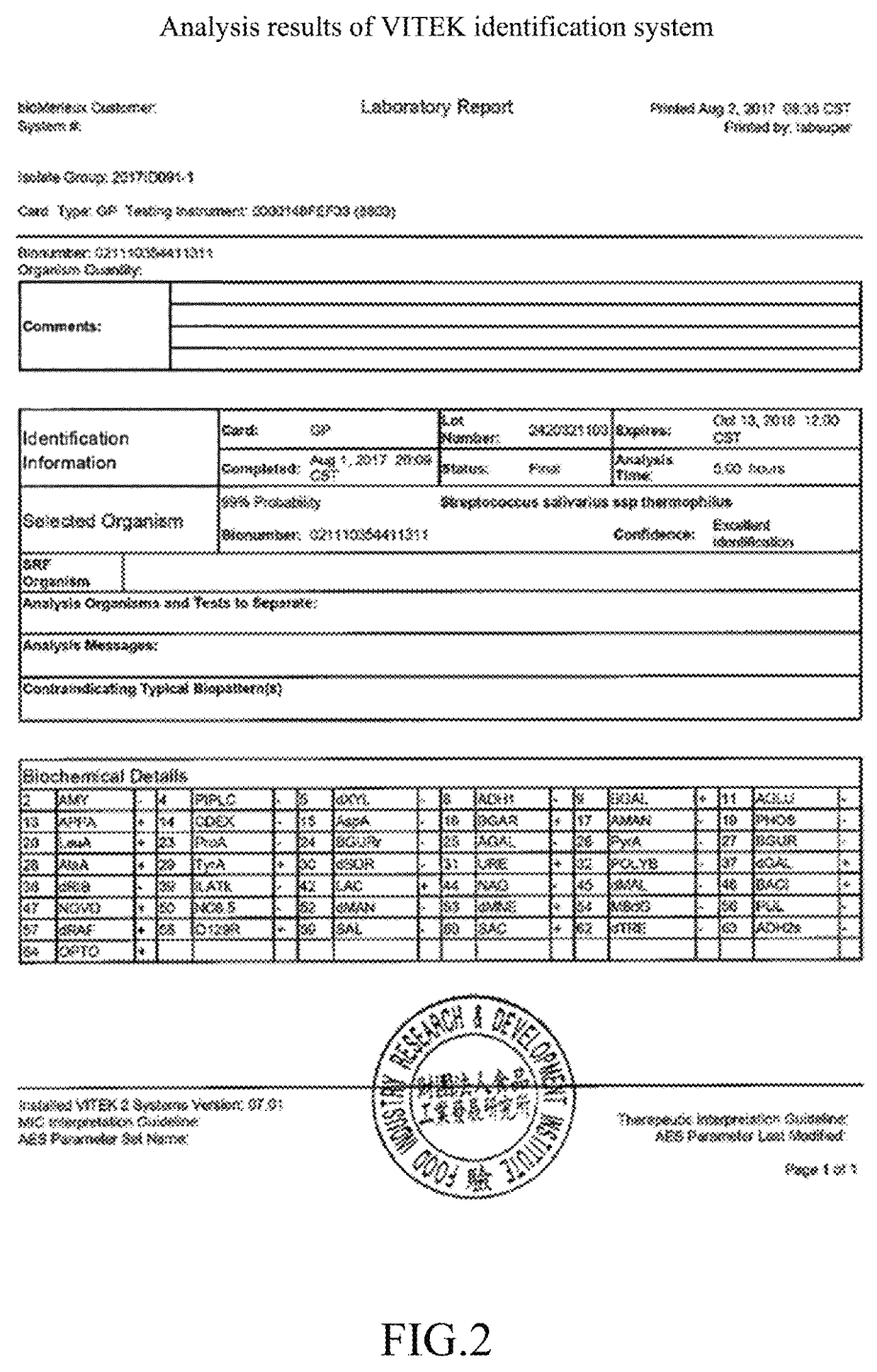

According to the analysis result of VITEK semi-automatic identification system, the *Streptococcus thermophilus* strain ST4 was closest to *Streptococcus salivarius* subsp. Thermophiles, and the similarity was up to 99%, as shown in FIG. 2.

According to the 16S rDNA sequencing identification, VITEK alignment results, and Approved Lists of Bacterial Names 1980 announced by The International Committee on Systematics of Prokaryotes, the *Streptococcus thermophilus* strain ST4 should be *Streptococcus* thermophiles (having a synonym of *Streptococcus salivarius* subsp. *thermophilus*).

Example 4 Inhibition of TNF-α Secretion by *Streptococcus thermophilus* Strain ST4

4.1 Preparation of Heat-Inactivated Bacterial Cells of *Streptococcus thermophilus*

The *Streptococcus thermophilus* strains ST4, s1, s2, s3 and BCRC13869 were cultured respectively and statically in Brain heart infusion (BHI) culture solutions at 37° C. for 24 hours and then the culture solutions were centrifuged (4000 RCF, 10 minutes). After the supernatant was removed, the remaining was washed with phosphate buffer saline (PBS), and then repeated the centrifugation and wash processes under the same conditions for two times. The bacterial cells suspended in PBS after cleaning were measured for the absorbance value with a spectrophotometer, put in a 70° C. water bath for 30 minutes, and finally cryopreserved at −20° C. for later use. The prepared samples were inoculated respectively into the BHI culture solutions and cultured at 37° C. for two days. As a result, there was no sign of growth, indicating that the bacteria had all died out.

4.2 Design of Cell Experiments

The human mononuclear THP-1 cell line (BCRC 60430) was purchased from Bioresource Collection and Research Center (Hsinchu, Taiwan), and cultured in RPMI 1640 broth containing 10% fetal bovine serum, 0.05 mM 2-mercaptoethanol, 10,000 I.U./mL penicillin, 10,000 μg/mL streptomycin and 25 μg/mL amphotericin at 37° C. under 5% $CO_2$. THP-1 cells were inoculated into a 96-well dish at a concentration of $6\times10^5$/mL, cultured for 18 hours, and then stimulated with 500 ng/mL LPS for 20 hours in the presence of the heat-inactivated bacterial cells of *Streptococcus thermophilus* (the absorbance value being adjusted to a final concentration of OD600=0.01). The culture supernatant was collected and analyzed for the content of cytokine TNF-α. For the LPS group, LPS was added alone for stimulation without the presence of bacterial cells. For the control group, only cell culture fluid was used.

4.3 Inhibition of Secretion of Inflammatory Cytokine TNF-α by *Streptococcus thermophilus* Strains ST4

Figure 3:
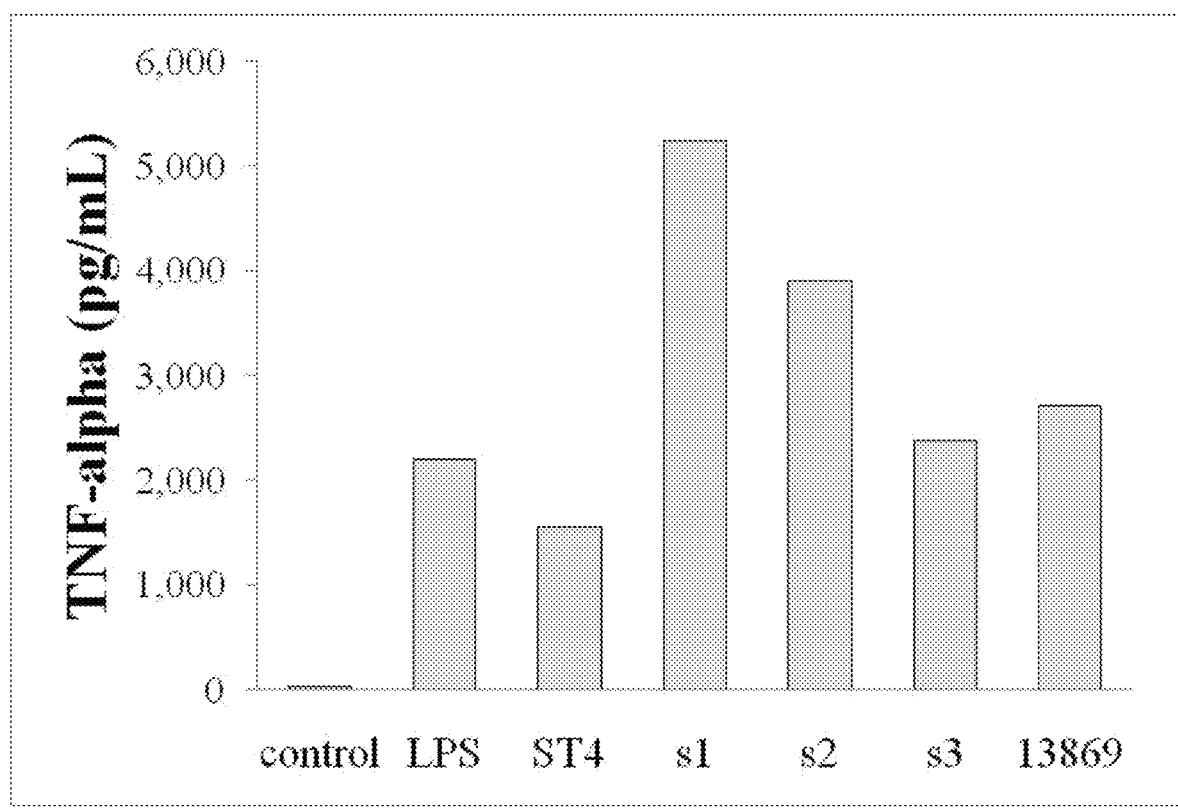
FIG. 3 shows that *Streptococcus thermophilus* strain ST4 reduces the number of azoxymethane/dextran sulfate sodium (AOM/DSS)-induced colorectal tumors (*$p<0.05$, **$p<0.01$).

FIG. 3 shows that the TNF-α secretion by THP-1 cells is promoted in the presence of heat-inactivated bacterial of *Streptococcus thermophilus* strains s1, s2, s3 and BCRC13869, while the TNF-α secretion by THP-1 cells is inhibited in the presence of heat-inactivated bacteria of *Streptococcus thermophilus* strains ST4. The results show that the heat-inactivated bacteria cells of strain ST4 reduce the LPS-induced TNF-α secretion by monocyte cells, indicating the anti-inflammatory activities of ST4.

Example 5 Prevention of Colorectal Cancer by *Streptococcus thermophilus* Strains ST4

5.1 Design of Animal Experiments

The animals for experiments were five-week-old ICR male mice (28~30 g). The mice for experiments were randomly divided into three groups at six weeks of age, namely the control group, AOMDSS group and ST4 group. Each group has 4 mice for experiments, and all groups were fed ad libitum with general commercial formula (Laboratory Rodent Diet. 5001). This experiment took the disease prevention model. First, the test sample was administrated, and then the occurrence of colorectal cancer was induced. After the mice were divided into groups, the control group and AOMDSS group were fed with PBS by tubes, and the ST4 group was fed with $1\times10^8$ CFU/day/mouse of *Streptococcus thermophilus* ST4 by tubes for 15 weeks, 5 days per week, and then sacrificed. The intestinal tissue was taken during sacrifice to measure length and weight. After feeding the test samples for one week, each mouse in the AOMDSS group and ST4 group was intraperitoneally injected with 10 mg/kg body weight of the mutagenic agent azoxymethane (AOM). After another week, the drinking water was added with 2.5% of the agent causing large intestinal ulcer, i.e. dextran sulfate sodium (DSS), was given for 7 consecutive days, and then ordinary drinking water was provided for 14 days. Afterwards, 2.5% DSS was given again for 7 days to induce colorectal cancer, and finally ordinary drinking water was provided until sacrifice. The control group was intraperitoneally injected with PBS, and DSS was not added to its drinking water.

5.2 Statistical Methods

The data is expressed as mean±standard deviation (Mean±SD). The difference between the groups is determined statistically significant or not by Student's t-test. When $p<0.05$ (*) or $p<0.01$ (**), the difference between the AOMDSS group and other groups was considered statistically significant.

5.3 Reduction of the Number of AOM/DSS-Induced Colorectal Tumors by *Streptococcus thermophilus* Strains ST4

Figure 4:
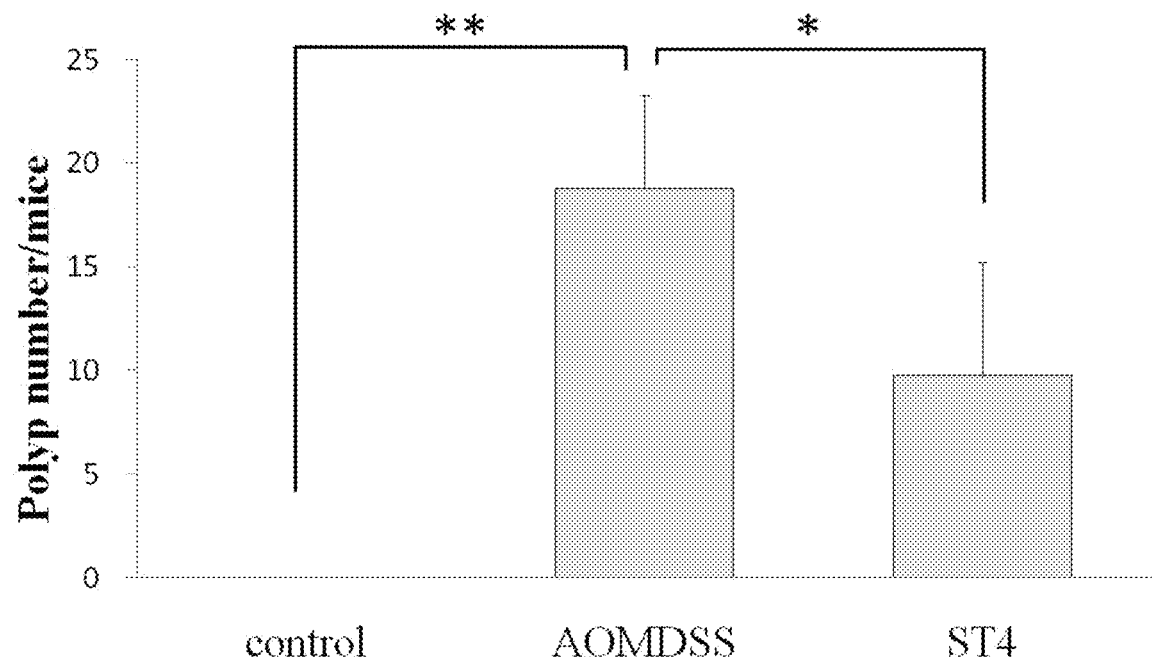
FIG. 4 shows that *Streptococcus thermophilus* strain ST4 reduces the number of (AOM/DSS)-induced colorectal tumors.

As shown in FIG. 4, compared with the control group, the AOMDSS group can significantly induce tumorigenesis of large intestine, indicating that the mutagen can induce tumorigenesis under the inflammatory condition of large intestine. The number of colorectal tumors of the ST4 group was significantly less than that of the AOMDSS group, which means oral ST4 has the effect of preventing colorectal cancer.

5.4 Relief of AOM/DSS-Caused Intestinal Inflammation by *Streptococcus Thermophilus* Strains ST4

Figure 5:
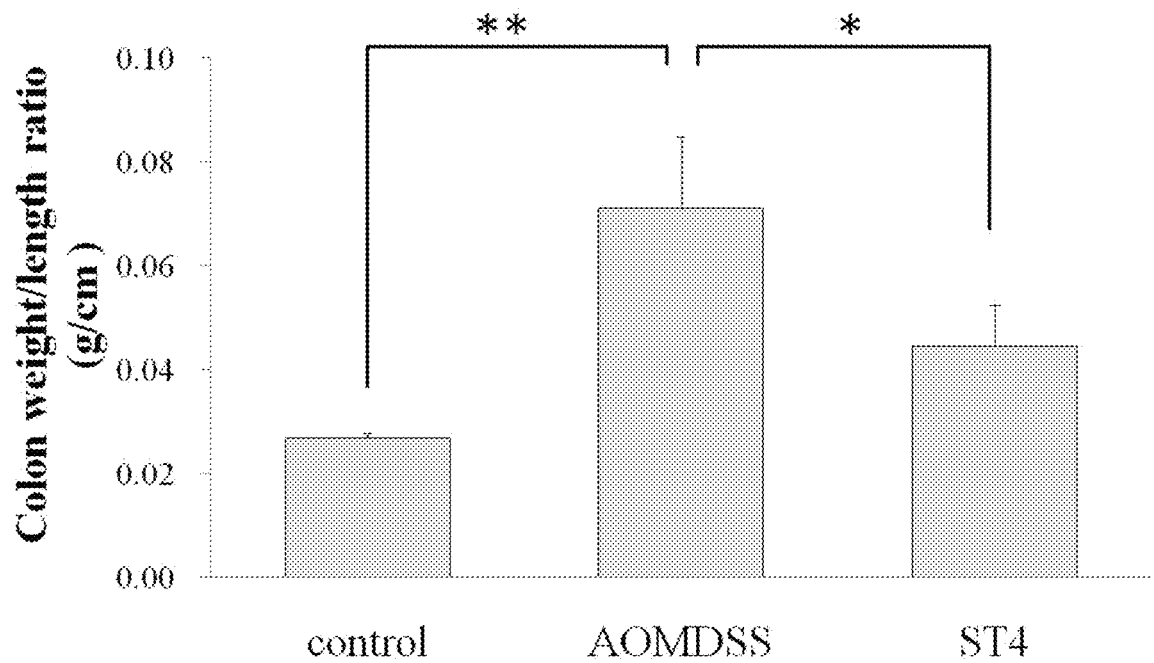
FIG. 5 shows that *Streptococcus thermophilus* strain ST4 relieves (AOM/DSS)-caused intestinal inflammation.

As shown in FIG. 5, as compared with the control group, AOMDSS treatment would significantly increase the gut weight/length ratio, indicating that AOMDSS treatment will cause intestinal inflammation. However, the gut weight/length ratio of the ST4 group was significantly lower than that of the AOMDSS group, indicating that oral ST4 can relieve intestinal inflammation.

People having ordinary skill in the art will understand that modifications can be made to the specific embodiments described above without departing from their broad inventive concepts. Therefore, it should be understood that the present invention is not limited to the disclosed specific embodiments, but is intended to cover modifications within the spirit and scope of the present invention defined by the appended claims.

What is claimed is:

1. A method for treating an inflammatory disease or a cancer, which comprises
    administering to a subject in need thereof an effective amount of a strain ST4 that was deposited at Deutsche Sammlung von Mikroorganismen and Zellkulturen GmbH with deposit number DSM33165 on May 28, 2019.

2. The method of claim 1, wherein the strain ST4 inhibits the production of TNF-α in said subject.

3. The method of claim 1, wherein the cancer is selected from the group consisting of colorectal cancer, esophageal cancer and gastric cancer.

4. The method of claim 1, wherein the strain ST4 is heat-inactivated.

* * * * *